United States Patent [19]
Horrobin

[11] Patent Number: 5,763,484
[45] Date of Patent: Jun. 9, 1998

[54] LIPIDS FOR TREATMENT OF DISEASE

[75] Inventor: David F. Horrobin, Guildford, England

[73] Assignee: Scotia Holdings plc, Guildford, United Kingdom

[21] Appl. No.: 823,790

[22] Filed: Mar. 24, 1997

Related U.S. Application Data

[60] Continuation of Ser. No. 482,446, Jun. 7, 1995, abandoned, which is a division of Ser. No. 197,459, Feb. 16, 1994, abandoned, which is a continuation of Ser. No. 13,163, Feb. 2, 1993, abandoned, which is a continuation of Ser. No. 810,434, Dec. 19, 1991, abandoned, which is a continuation of Ser. No. 668,700, Mar. 7, 1991, abandoned, which is a continuation of Ser. No. 522,085, May 11, 1990, abandoned, which is a continuation of Ser. No. 274,358, Nov. 21, 1988, abandoned, which is a division of Ser. No. 45,545, May 4, 1987, Pat. No. 4,806,569, which is a division of Ser. No. 575,744, Jan. 31, 1984, Pat. No. 4,681,896.

[30] Foreign Application Priority Data

Feb. 1, 1983 [GB] United Kingdom .................... 8302708

[51] Int. Cl.$^6$ .................................................... A61K 31/20
[52] U.S. Cl. ............................................................ 514/560
[58] Field of Search ................................................ 514/560

[56] References Cited

U.S. PATENT DOCUMENTS 3,950,547  4/1976  Lamar et al. ........................... 426/74
4,058,594  11/1977  Williams ................................. 424/490

OTHER PUBLICATIONS

Müller *Das Deutsche Gesundheitswesen* 1973, 28(35), 1633–1638.

*Primary Examiner*—Kathleen K. Fonda
*Attorney, Agent, or Firm*—Banner & Witcoff, Ltd.

[57] ABSTRACT

A method of treatment of a disorder, including breast cancer and other cancer, with effective amounts of one or more of the metabolites of linoleic acid (GLA, DGLA, AA, 22:4n-y or 22:5n-6) and one or more of the metabolites of α-linolenic acid (18:4n-3, 20:4n-3, 20:5n-3, 22:5n-3 or 22:6n-3) administered as such or in the form of an ester, salt, amide or other derivative convertible in the body thereto alone or in acceptable pharmaceutical carrier or diluent.

1 Claim, No Drawings

LIPIDS FOR TREATMENT OF DISEASE

This is a continuation of Ser. No. 08/482,446, filed Jun. 7, 1995, now abandoned; which is a division of Ser. No. 08/197,459, filed Feb. 16, 1994, now abandoned; which is a continuation of Ser. No. 08/013,163, filed Feb. 2, 1993, now abandoned; which is a continuation of Ser. No. 07/810,434, filed Dec. 19, 1991, now abandoned; which is a continuation of Ser. No. 07/668,700, filed Mar. 7, 1991, now abandoned; which is a continuation of Ser. No. 07/522,085, filed May 11, 1990, now abandoned; which is a continuation of Ser. No. 07/274,358, filed Nov. 21, 1988, now abandoned; which is a division of Ser. No. 07/045,545, filed May 4, 1987, now U.S. Pat. No. 4,806,569; which is a division of Ser. No. 06/575,744, filed Jan. 31, 1984, now U.S. Pat. No. 4,681,896.

FIELD OF THE INVENTION

This invention relates to the treatment of certain diseases and disorders primarily, but not exclusively, in the field of human medicine and to compositions for use therein.

GENERAL BACKGROUND

The essential fatty acids (EFAs) are of two types, the n-3 (or ω-3) series derived from α-linolenic acid and the n-6 (or ω-6) series derived from linoleic acid. Linoleic acid and α-linolenic acid are like vitamins in that they cannot be manufacturered in the body and therefore must be provided in the diet. The body can metabolise them along the pathways below and such metabolism is believed to be essential if they are to fulfil their functions. The pathways are:

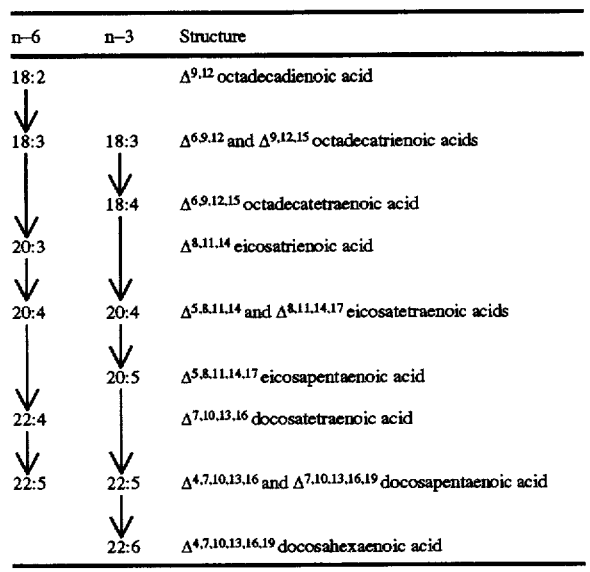

| n-6 | n-3 | Structure |
|---|---|---|
| 18:2 | | $\Delta^{9,12}$ octadecadienoic acid |
| 18:3 | 18:3 | $\Delta^{6,9,12}$ and $\Delta^{9,12,15}$ octadecatrienoic acids |
| | 18:4 | $\Delta^{6,9,12,15}$ octadecatetraenoic acid |
| 20:3 | | $\Delta^{8,11,14}$ eicosatrienoic acid |
| 20:4 | 20:4 | $\Delta^{5,8,11,14}$ and $\Delta^{8,11,14,17}$ eicosatetraenoic acids |
| | 20:5 | $\Delta^{5,8,11,14,17}$ eicosapentaenoic acid |
| 22:4 | | $\Delta^{7,10,13,16}$ docosatetraenoic acid |
| 22:5 | 22:5 | $\Delta^{4,7,10,13,16}$ and $\Delta^{7,10,13,16,19}$ docosapentaenoic acid |
| | 22:6 | $\Delta^{4,7,10,13,16,19}$ docosahexaenoic acid |

The acids are in the natural all-cis configurations. In the n-6 series commonly used names for the 18:2, 18:3, 20:3, 20:4 and 22:4 acids are oleic acid, γ-linolenic acid (GLA), dihomo-γ-linolenic acid (DGLA), arachidonic acid (AA) and adrenic acid. In the n-3 series only α-linolenic acid (18:3) is commonly referred to by a non-systematic name.

The elongation stages in the natural metabolic pathway are much more rapid than the desaturations. The sequence believed to be mediated by common enzymes in the two pathways, are:

| n-6 | | n-3 |
|---|---|---|
| 18:2 | $\Delta^6$ desaturase | 18:3 |
| 18:3 | elongation | 18:4 |
| 20:3 | $\Delta^5$ desaturase | 20:4 |
| 20:4 | elongation | 20:5 |
| 22:4 | $\Delta^4$ desaturase | 22:5 |
| 22:5 | | 22:6 |

The n-3 acids are metabolised preferentially and as a result plasma levels of 18:3 are low and 18:4 and 20:4 are in trace amounts only. In contrast the n-6 acids are all normally detectable, though 18:3 is at low levels, being apparently converted to 20:3 more rapidly than its relatively slow production from 18:2.

METABOLIC DEFECTS

Atopy is an inherited tendency to develop one or more of a group of diseases of which eczema, asthma and allergic rhinitis are the major ones. Some people have only eczema, some have only asthma or rhinitis, some have two or more of the conditions, some have none but may have children who have one of the problems. Atopy is associated with abnormal immune responses and it is generally believed that in order to develop a clinical disease one must have the inherited abnormality in immune responsitveness, coupled with exposure to some environmental factor which brings out that abnormality. People with atopic inheritance who are lucky enough not to be exposed to the environmental factor will not develop any obvious illness but may pass on the abnormality to their children. The precise mode of inheritance is not clear. A number of allergens and environmental factors which can trigger clinical atopic disease are known but it is likely that many more are not. Epidemiological surveys have shown that migraine, Crohn's disease, ulcerative colitis, otitis media and nephrotic syndrome are all considerably, commoner in peoples with than in those without atopy. The presense of atopy greatly increases the risk of developing one of these conditions.

We have found that humans with atopic eczema have a defect in conversion of linoleic acid to GLA. While linoleic acid levels are normal or elevated, levels of DGLA and AA are low, indicating a block in the first step of the n-6 metabolic pathway. Administration of GLA in the form of Evening Primrose oil partially corrects the deficits in DGLA and AA.

We have also found that patients with painful lumpy breasts, not caused by breast cancer, (benign breast disease) have normal or elevated levels of linoleic acid and low levels of DGLA, AA, 22:4n-6 and 22:5n-6. Administration of GLA in the form of Evening Primrose oil partly corrects the biochemical deficits and produces clinical improvement, especially in those patients whose breast condition worsened before each menstrual period. Patients who had breast problems unrelated to menstruation showed a lesser response.

We have, further, analysed blood samples from patients with atopic eczema and benign breast disease and have found that while α-linolenic acid levels are normal, levels of the long chain n-3 acids, 20:5n-3, 22:5n-3 and 22:6n-3 are low, especially in patients with breast disease not related to menstruation. Figures for eczema and asthma for example are (plasma phospholipids):

| Fatty acid | Normal | Asthma | Eczema |
|---|---|---|---|
| 18:2n-6 | 21.45 ± 2.81 | 21.99 ± 3.31 | 24.50 ± 3.42xx |
| 18:3n-6 | 0.16 ± 0.12 | 0.22 ± 0.31 | ndxxx |
| 20:3n-6 | 3.06 ± 0.60 | 2.96 ± 0.55 | 2.63 ± 0.52x |
| 20:4n-6 | 11.36 ± 1.67 | 9.18 ± 1.39xxx | 6.75 ± 1.12xxx |
| 22:4n-6 | 0.73 ± 0.26 | 0.14 ± 0.22xxx | 0.38 ± 0.24xx |
| 22:5n-6 | 1.12 ± 0.67 | ndxxx | 0.13 ± 0.09xx |
| 18:3n-3 | 0.27 ± 0.53 | 0.38 ± 0.15 | 0.36 ± 0.17 |
| 20:5n-3 | 1.01 ± 0.36 | 1.19 ± 0.44 | 0.75 ± 0.57xx |
| 22:5n-3 | 0.93 ± 0.27 | 1.22 ± 0.23xxx | 0.74 ± 0.19xxx |
| 22:6n-3 | 3.54 ± 0.89 | 3.88 ± 0.99x | 2.43 ± 0.62xxx |

Difference probabilities (Student's t test)

x $p < 0.01$
xx $p < 0.001$
xxx $p < 0.0001$

Figures for benign breast disease are for example:

| Fatty acid | Control | Non-cyclical breast disease |
|---|---|---|
| 18:2n-6 | 21.45 ± 0.84 | 22.33 ± 0.89 |
| 20:3n-6 | 3.06 ± 0.09 | 2.54 ± 0.14 |
| 20:4n-6 | 11.36 ± 0.24 | 7.69 ± 0.36 |
| 22:4n-6 | 0.73 ± 0.04 | 0.33 ± 0.05 |
| 22:5n-6 | 1.12 ± 0.09 | 0.73 ± 0.09 |
| 18:3n-3 | 0.27 ± 0.11 | 0.26 ± 0.03 |
| 20:5n-3 | 1.01 ± 0.05 | 0.96 ± 0.08 |
| 22:5n-3 | 0.93 ± 0.04 | 0.68 ± 0.09 |
| 22:6n-3 | 3.54 ± 0.13 | 2.28 ± 0.15 |

The method of determination was: Plasma samples (1 ml) were extracted with chloroform:methanol (2:1). The extract was filtered through sodium sulphate, evaporated to dryness, and taken up in 0.5 ml chloroform:methanol. The lipid fractions were separated by thin layer chromatography on silica gel plates. The phospholipid fraction, taken to reflect essential fatty acid changes most sensitively, was methylated using boron trifluoride-methanol. The resulting methyl esters of the fatty acids were separated and measured using a Hewlett Packard 5880 gas chromatograph with a six foot column packed with 10% silar on chromosorb WAW 106/230. The carrier gas was helium (30 mL/min). Oven temperature was programmed to rise from 165° C. to 190° C. at 2° C. min. Detector temperature was 220° C. and injector temperature 200° C. Retention times and peak areas were automatically computed by a Hewlett Packard Level 4 integrator. Peaks were identified by comparison with standard fatty acid methyl esters. Thus patients with these disorders are deficient not only in the long chain EFAs of the n-6 series but also in the long chain EFAs of-the n-3 series, and full correction of symptoms requires correction of both deficiencies. We believe that such combined deficiencies are a general feature of patients with atopic disorders and disorders associated with atopy, of patients with benign breast disease, of patients with breast cancer (which is commoner where there is pre-existing non-cancerous breast disease) and cancers generally, and of patients with other disorders associated with defects in metabolism of n-6 fatty acids. Such disorders include, alcoholism, and diabetes which interfere with the conversion of linoleic acid to GLA. There is for example strong evidence that the conversion of linoleic acid to GLA is restricted or absent in cancer cells. Further, in normal tissues the same enzyme converts linoleic acid to GLA as desaturates α-linolenic acid to form 18:4n-3. In both cases the activity is a Δ-6-desaturase activity and the presence of either one of the acids inhibits the desaturation of the other. Thus, cancer cells, and any other cells where the Δ-6 desaturase activity is low and particularly those of alcoholic and diabetic patients are going to be deficient in the metabolites of α-linoleic acid.

THEORY

The invention lies in the method and compositions proposed herein, but without limitation to any theory it follows from the discussion above that there are two basic rationales.

A. Correction of deficiency. If levels of normal body constituents are below normal in a disease situation then it is a reasonable proposition that those low levels are contributing to and perhaps causing the disease and therefore that they should be corrected. We have demonstrated that abnormal levels of high fatty acids are indeed present in the conditions discussed herein.

B. Correction of a 1-series/2-series PG balance. As appears from many earlier patent applicatins and other publications of work by the inventor, the actions of the 1-series PG's and other metabolic products derived from DGLA are almost all either desirable or neutral, but the actions of the 2-series PG's and other metabolic products derived from arachidonic acid are very mixed, some being desirable and some being highly undesirable. Studies of the interactions between the metabolism of the n-6 acids and that of the n-3 acids have shown that elongation reactions (e.g. GLA to DGLA) are highly efficient and there is very little competition either way. In contrast, the two series of fatty acids compete with one another effectively for the desaturation processes. This means that the n-3 fatty acids will interfere with both Δ-6 and Δ-5 desaturation in the n-6 series. This competition seems to occur even when the n-3 fatty acid is not actually a substrate for the enzyme concerned. For example, 20:5n-3 competitively inhibits Δ-6 desaturation. A consequence of this is that the presence of n-3 fatty acids in a combination will lead to some inhibition of the conversion of DGLA to arachidonic acid by the Δ-5-desaturase. As a result of the presence of the n-3 EFAs, the efficiency of either GLA or DGLA in increasing the ratio of DGLA products to arachidonic acid products will therefore be increased. The present invention thus complements earlier patents of the inventor's in which emphasis is laid on 1-series/2-series PG balance, in view of which GLA and DGLA are the preferred n-6 acids for use in the present invention.

DETAILED STATEMENT OF THE INVENTION

In the light of the discussion above the present invention may be summarised as:

(i) A method of treating atopic disorders, including eczema, asthma, allergies (especially allergic rhinitis), migraine and disorders associated with atopy including Crohn's disease, ulcerative colitis, otitis media, nephrotic syndrome, or benign breast disease, or breast or other cancer, or diabetes or alcoholism (including the effect both of ingestion of excess alcohol and of withdrawal) wherein one or more of the metabolites of linoleic acid (GLA, DGLA, AA, 22:4n-6, 22:5n-6) and one or more of the metabolites of α-linolenic acid (18:4n-3, 20:4n-3, 20:5n-3, 22:5n-3, 22:6n-3) are administered and (ii) Compositions of said metabolites when for such use. The acids may be administered in the form of the acid itself or as an ester, amide, salt or any other functional derivative capable of being converted to a biologically active form of the acid within the body and may be from natural or synthetic sources.

Most studies have shown that the metabolism of the n-3 EFAs is more efficient than that of the n-6 EFAS. Judging by their presence in various body tissues, the important n-3 EFAs are thus 20:5n-3 and 22:6n-3. One therefore wants most preferably to use combinations of either 18:4n-3 or 20:4n-3 which can give rise to 20:5n-3 and 22:6n-3, or of those acids themselves, with either GLA or DGLA.

Doses for each acid are from 1 mg to 50 g per day, preferably 50 mg to 5 g per day, conveniently in conventional gelatine capsules.

FORMS AND SOURCE OF γ-LINOLENIC AND OTHER ACIDS

Conventional sources of the acids include Evening Primrose (Oenothera) oil containing about 9% of GLA and oils from marine or migratory fish which contain substantial amounts of 20:5n-3 and 22:6n-3.

Suitable physiologically functional derivatives, convertible in the body to the acids to enter the metabolic pathways given earlier herein, are physiologically acceptable salts, esters (particularly glycerides and simple $C_1$–$C_4$ alkyl esters), amides and phospholipids. Indirect identification of useful derivatives is by their having the valuable effect in the body of the acid itself, but conversion can be shown directly by gas chromatographic analysis of concentrations in blood, body fat, or other tissue by standard techniques for example those of Pelick et al. p. 23, "Analysis of Lipids and Lipoproteins"Ed. Perkins, American Oil Chemists Society, Champaign, Ill., U.S.A.

DIETARY COMPOSITIONS

The invention is chiefly described in terms of use of pharmaceutical compositions, but it will be understood that the γ-linolenic and other acids being in the nature of dietary supplements, could be incorporated in a dietary margarine or other foodstuffs: use of such foodstuffs, possibly containing other active materials and generally referred to in this description as dietary or pharmaceutical compositions, are within the purview of the invention and thus of the term pharmaceutical compositions or the like used in the claims.

VETERINARY APPLICATIONS

It will be understood that where a disorder of a kind calling for treatment in animals arises, the invention while described primarily in terms of human medicine and treatment is equally applicable in the veterinary field.

PHARMACEUTICAL PRESENTATION

The compositions used according to the invention are conveniently in a form suitable for oral, rectal, parenteral or topical administration in a suitable pharmaceutical vehicle, as discussed in detail for example in U.K. Patent Specification No. 1 082 624 and in any case very well known generally for any particular kind of preparation. Thus for example tablets, capsules, ingestible liquid or powder preparations, creams and lotions for topical application, or suppositories, can be prepared as required. Injectable solutions of hydrolysed Oenothera oil may be prepared using albumin to solubilise the free acid.

Advantageously a preservative is incorporated into the preparations. α-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following are specific examples of the invention:

EXAMPLE 1

A capsule containing 60% Evening Primrose oil and 40% mackerel oil administered in 0.5 g capsules six times per day for the conditions listed herein.

EXAMPLE 2

A capsule containing 70% Evening Primrose oil and 30% salmon oil administered in 0.5 g capsules eight times per day for the conditions listed herein.

EXAMPLE 3

A 0.25 g capsule containing 150 mg of GLA and 100 mg of 20:5n-3 administered 3 times per day for the conditions listed herein.

EXAMPLE 4

A capsule containing 50 mg of DGLA, 50 mg of AA, 20 mg of 22:4n-6, 20 mg of 22:5n-6, 50 mg of 20:5n-3, 20 mg of 22:5n-3 and 20 mg of 22:6n-3 taken four times a day for the conditions listed herein.

What is claimed is:

1. A method for treating unsaturated fatty acid deficiencies in cancer patients comprising administering to cancer patients:
  (a) an effective amount of a metabolite of linoleic acid selected from the group consisting of GLA, DGLA, AA, a 22:4n-6 essential fatty acid and a 22:5n-6 essential fatty acid, and
  (b) an effective amount of a metabolite of alphalinoleic acid selected from the group consisting of 18:4n-3, 20:4n-3, 20:5n-3, 22:5n-3 and 22:6n-3 essential fatty acids.

* * * * *